(12) United States Patent
Gann et al.

(10) Patent No.: US 8,062,245 B2
(45) Date of Patent: Nov. 22, 2011

(54) SELF-ORIENTING APPLICATOR

(75) Inventors: Diana Lynn Gann, Lebanon, OH (US); Margaret Henderson Hasse, Wyoming, OH (US); Paul Gregory Methven, Loveland, OH (US); Kerry Lloyd Weaver, Florence, KY (US); Michael Sean Farrell, Terrace Park, OH (US); Dale Edwin Barker, Hamilton, OH (US); Dan Raymond Wiegele, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 836 days.

(21) Appl. No.: 11/703,919

(22) Filed: Feb. 8, 2007

(65) Prior Publication Data
US 2008/0195030 A1    Aug. 14, 2008

(51) Int. Cl.
*A61F 13/15* (2006.01)
*A61F 13/20* (2006.01)

(52) U.S. Cl. ............... 604/15; 604/385.18; 604/904

(58) Field of Classification Search .......... 604/11–18, 604/57–60, 385.17–385.18, 904
See application file for complete search history.

(56) References Cited

U.S. PATENT DOCUMENTS

| | | | |
|---|---|---|---|
| 3,424,159 A | 1/1969 | Whitehead et al. | |
| 3,643,661 A | 2/1972 | Crockford | |
| 3,674,026 A | 7/1972 | Werner et al. | |
| 3,765,417 A | 10/1973 | Crockford | |
| 3,831,605 A | 8/1974 | Fournier | |
| 3,971,378 A * | 7/1976 | Krantz | 604/369 |
| 4,048,998 A | 9/1977 | Nigro | |
| 4,198,978 A | 4/1980 | Nigro | |
| 4,291,696 A | 9/1981 | Ring | |
| 4,411,647 A * | 10/1983 | Sakurai et al. | 604/16 |
| 5,041,080 A | 8/1991 | Shimatani et al. | |
| 5,158,535 A | 10/1992 | Paul et al. | |
| 5,267,953 A | 12/1993 | Paul et al. | |
| 5,437,628 A | 8/1995 | Fox et al. | |
| 5,453,085 A | 9/1995 | Schoelling | |
| 5,788,910 A | 8/1998 | McNelis et al. | |
| 6,572,577 B1 | 6/2003 | Binner et al. | |
| 6,645,136 B1 | 11/2003 | Zunker et al. | |
| 6,648,846 B2 | 11/2003 | Binner et al. | |
| 6,923,789 B2 | 8/2005 | LeMay et al. | |
| 6,939,289 B2 | 9/2005 | Zunker et al. | |

(Continued)

FOREIGN PATENT DOCUMENTS
WO    WO 01/30291 A1    5/2001

OTHER PUBLICATIONS
PCT International Search Report dated Jan. 9, 2008.

*Primary Examiner* — Leslie Deak
*Assistant Examiner* — Philip R Wiest
(74) *Attorney, Agent, or Firm* — Andrew J. Hagerty; Amanda T. Barry (57) ABSTRACT

An applicator for a feminine hygiene product is provided. The applicator includes a barrel portion, a grip portion, and a plunger. The barrel portion can be rotatably connected to the grip portion, wherein the barrel portion is adapted to rotate relative to the grip portion. Also provided is a method for orienting a feminine hygiene product within a vagina.

10 Claims, 7 Drawing Sheets

U.S. PATENT DOCUMENTS

| | | |
|---|---|---|
| 6,958,057 B2 | 10/2005 | Berg, Jr. et al. |
| 7,014,637 B1 | 3/2006 | Denti et al. |
| 7,044,928 B2 * | 5/2006 | LeMay et al. .......... 604/15 |
| 7,081,110 B2 | 7/2006 | Karapasha |
| 2002/0010413 A1 | 1/2002 | Binner et al. |
| 2003/0040695 A1 | 2/2003 | Zhao et al. |
| 2003/0073947 A1 | 4/2003 | Binner et al. |
| 2003/0073948 A1 | 4/2003 | Binner et al. |
| 2003/0125658 A1 | 7/2003 | Marvin |
| 2003/0216680 A1 | 11/2003 | Binner et al. |
| 2004/0078013 A1 | 4/2004 | Zunker et al. |
| 2005/0256483 A1 | 11/2005 | Przepasniak et al. |
| 2005/0273041 A1 | 12/2005 | Osborn, III et al. |
| 2006/0004320 A1 | 1/2006 | Berg, Jr. et al. |
| 2007/0032758 A1 | 2/2007 | Chase et al. |

* cited by examiner

SELF-ORIENTING APPLICATOR

FIELD OF THE INVENTION

The present invention relates generally to self-orienting applicators, more specifically to self-orienting applicators for feminine hygiene products.

BACKGROUND OF THE INVENTION

Feminine hygiene products, such as tampons and pessaries, are generally used by women within the vagina for feminine needs, such as, e.g., to absorb menstrual or other body exudates, for pelvic support, and/or for other feminine needs. Such feminine hygiene products can be inserted into the vagina digitally, such as, e.g., by using a finger, or can be inserted into the vagina by using an applicator.

It is a common misconception that the vagina is shaped like a cylindrical tube. In actuality, the vagina is a pocket that is irregular in shape. When not distended by a foreign object, the vagina may resemble a pear shape in appearance when viewed from the coronal or front view of the female anatomy. From the sagittal or side view, the vagina is a long, thin muscular structure. Menstrual fluid typically enters the vagina through the cervix, which is generally located near the top of the vagina where the vagina is widest.

Currently available catamenial tampons are typically in the form of a circular cylinder prior to insertion in the vagina. Such tampons are generally formed from pledgets larger in size than the vaginal orifice. The pledgets are compressed to a smaller, cylindrical form with a circular cross-sectional shape in order to facilitate insertion into the vagina via the relatively narrow introitus. As fluid is absorbed from the vagina, these tampons are intended to re-expand toward their original pre-compressed size to eventually effectively cover the vaginal cavity against fluid leakage or bypass; however, such tampons can fail to re-expand sufficiently or fast enough to provide good coverage and thus can fail to provide sufficient leakage protection. As a result, menstrual fluid can bypass the tampon and leak outside the user's body.

Therefore, it would be desirable to provide a tampon with non-uniform expansion, such as, e.g., improved expansion characteristics in the width direction. Tampons having improved expansion in the width direction can be difficult to orient within the vagina such that the area of greatest expansion will correspond to the width of the vagina. For example, current applicators are generally opaque and circular in cross-sectional shape and thus can hide the tampon and any potential orientation, making it invisible to the user. As such, the user typically would have no indication that orientation is possible.

Even if an applicator having a non-circular cross-sectional shape were provided, the user can often be unaware that orientation of the applicator and/or tampon can affect performance. A logical orientation for a non-circular applicator is parallel to the external genitalia or labia, such that the larger width of the applicator runs front to back of the body. The vagina, however, transitions from the introitus within the body such that its larger dimension runs side to side. As a result, the logical orientation of an applicator according to the external genitalia would position the tampon with its area of greatest expansion perpendicular to the width of the vagina instead of aligned with the width of the vagina, as intended.

As such, it would be desirable to provide an applicator for properly orienting a feminine hygiene product within the vagina of a user.

SUMMARY OF THE INVENTION

A self-orienting applicator, such as, e.g., for a feminine hygiene product, is provided. The applicator includes a barrel portion, a grip portion, and a plunger. The barrel portion can be rotatably connected to the grip portion, wherein the barrel portion is adapted to rotate relative to the grip portion.

Also provided is a method for orienting a feminine hygiene product within a user's vagina having a vaginal width and a vaginal thickness, the vaginal width being greater than the vaginal thickness. The method includes providing an applicator comprising a barrel portion, a grip portion, and a plunger, the barrel portion having a barrel width and a barrel thickness, the barrel width being greater than the barrel thickness, the barrel portion being rotatably connected to the grip portion, wherein the barrel portion is adapted to rotate relative to the grip portion, the barrel portion enclosing a feminine hygiene product having a product width and a product thickness, the product width being greater than the product thickness; grasping the applicator by holding the grip portion; inserting the barrel portion into the vagina such that the barrel portion rotates relative to the grip portion; depressing the plunger to expel the feminine hygiene product from the applicator; and removing the applicator from the vagina.

A process for preparing an applicator for a feminine hygiene product is also provided.

DETAILED DESCRIPTION OF THE INVENTION

The present invention relates to applicators for properly orientating feminine hygiene products, such as, e.g., tampons and/or pessaries, within a user's body. It can be difficult to determine the proper orientation of feminine hygiene products with non-uniform expansion, such as, e.g., products that expand widthwise, which can result in users inadvertently inserting the product such that the maximum expansion occurs perpendicular to the greatest vaginal width instead of aligned with the greatest vaginal width as intended. As such, the present invention relates to applicators including a barrel portion that can rotate relative to the grip portion of the applicator such that the feminine hygiene product is oriented in the user's body during and/or after insertion, such as, for example, via body pressure upon the applicator during insertion of the feminine hygiene product. In certain embodiments, the applicators can be used with feminine hygiene products having a non-uniform expansion, such as, e.g., a widthwise expansion. Feminine hygiene products with a non-uniform expansion can include, for example, tampons that are formed with a non-circular cross-sectional shape, such as, e.g., tampons with a somewhat or substantially oval cross-sectional shape, and/or tampons that are formed with a circular or nearly circular cross-sectional shape having more compression and/or potential expansion in the width direction than in the thickness or length direction.

As used herein, the term "feminine hygiene product" refers to absorbent articles useful for feminine hygiene, such as articles that typically can be intended for feminine use internally, such as, e.g., within a user's vagina. Internal feminine hygiene products include, for example, tampons and pessaries.

As used herein, the term "tampon" refers to any type of absorbent structure that can be inserted into the vaginal canal or other body cavity, such as, e.g., for the absorption of fluid, to aid in wound healing, and/or for the delivery of materials, such as moisture or active materials such as medicaments. In general, the term "tampon" is used to refer to a finished tampon after the compression and/or shaping process.

As used herein, the term "pledget" refers to an absorbent material prior to the compression and/or shaping of such construction into a tampon.

As used herein, the term "pessary" refers to any type of substantially non-absorbent structure for the purpose of reducing urine leakage and/or supporting a prolapsed uterus and/or bladder. Such pessaries can have any variety of shapes and sizes including cylinder, ovate, spherical, tubular, annual rings, "U" shaped, cup shaped, rings, cubes or donut shaped, and can function in any suitable manner, such as, e.g., by direct application of support, lever force, expansion of the device by selection of material, and/or by inflation of the device.

As used herein, the term "vaginal canal" refers to the internal genitalia of the human female in the pudendal region of the body. The terms "vaginal canal" or "within the vagina" as used herein are intended to refer to the space located between the introitus of the vagina (sometimes referred to as the sphincter of the vagina) and the cervix.

As used herein, "applicator" refers to a device or implement that facilitates the insertion of a tampon or pessary into an external orifice of a mammal. Exemplary applicators include telescoping, tube and plunger, and compact applicators.

As used herein, the term "insertion end" refers to the portion of the tampon including the end that is intended to enter the vaginal canal first when inserting the tampon.

As used herein, the term "withdrawal end" refers to the portion of the tampon opposite the insertion end including the end is intended to exit the vaginal canal first when the tampon is removed from the vagina.

As used herein, the term "rotatably connected" refers to configurations in which a first element is directly attached to a second element in a rotatable manner, such as, e.g., in a manner that allows for rotation of the first element with respect to the second element or vice versa, and configurations in which the first element is indirectly attached to a second element in a rotatable manner by affixing the first element to intermediate member(s) that in turn are affixed to the second element.

As used herein, the term "securely connected" refers to configurations in which a first element is directly attached in a substantially stationary manner to a second element by affixing the first element directly to the second element, configurations in which the first element is indirectly attached in a substantially stationary manner to the second element by affixing the first element to intermediate member(s) that in turn are affixed to the second element, and configurations in which the first element is integral with the second element, such as, for example, when the first element is an extension of the second element.

As used herein, the term "length" of an applicator refers to the longest linear dimension of the applicator.

As used herein, the term "cross-section" of an applicator refers to a section orthogonal to the length.

As used herein, the term "generally non-circular cylindrical" excludes the usual shape of tampons having a generally circular cross-section and resembling a circular cylinder, such as tampons marketed today. The term "generally non-circular cylindrical" can include generally elliptical, oval, oblate, or partially flattened cylinders, curved cylinders, and shapes that have varying cross-sectional areas.

Figure 1:
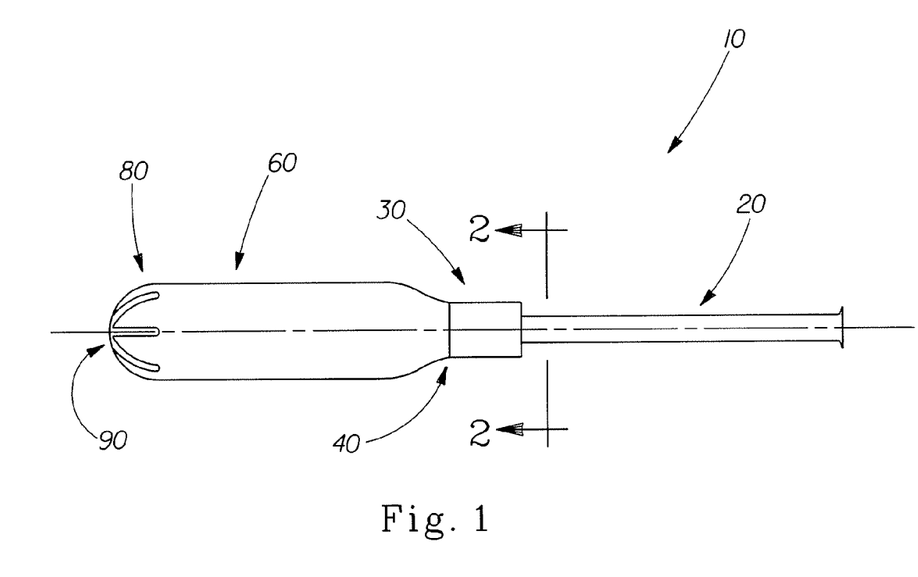
FIG. 1 is a plan view of one embodiment of the present invention.

FIG. 1 shows a plan view of one embodiment of the invention. The applicator 10 has a plunger 20, a grip portion 30, and a barrel portion 60. The barrel portion 60 can contain a tampon prior to depression of the plunger 20. In this embodiment, the grip portion 30 is rotatably connected to the barrel portion 60. For example, the barrel portion 60 can rotate relative to the grip portion 30, such as, e.g., when the grip portion 30 is held stationary by the user. The applicator 10 has a length L. As shown in FIG. 1, in certain embodiments, the barrel portion 60 and grip portion 30 can be non-continguous, for example, the barrel portion 60 and the grip portion 30 can be separated by a split 40, which can allow the barrel portion 60 to rotate relative to the grip portion 30. The plunger 20 can be telescopically and/or slidably mounted in the barrel portion 60. In certain embodiments, the insertion end 80 can include petals 90.

Figure 2:
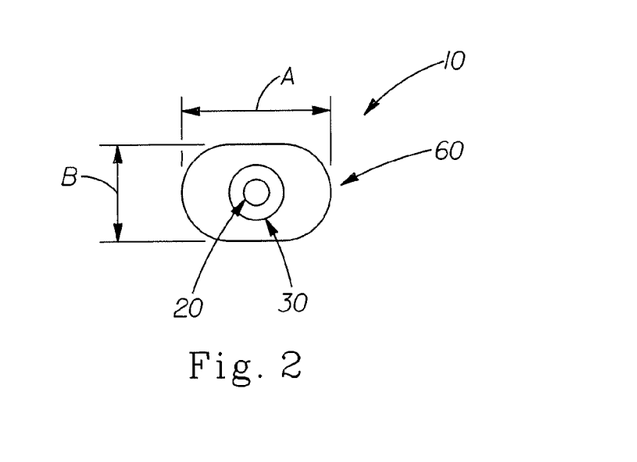
FIG. 2 is a cross-sectional view along section 2-2 of FIG. 1.

FIG. 2 shows a cross-sectional view along section 2-2 of FIG. 1. The applicator 10 shown has a plunger 20, a grip portion 30, and a barrel portion 60. In this embodiment, the barrel portion 60 is oval, while the plunger 20 and grip portion 30 are cylindrical. The applicator 10 shown has a width A and a thickness B running perpendicular to the length L and to each other. In certain embodiments, the width A is larger than the thickness B.

Figure 3:
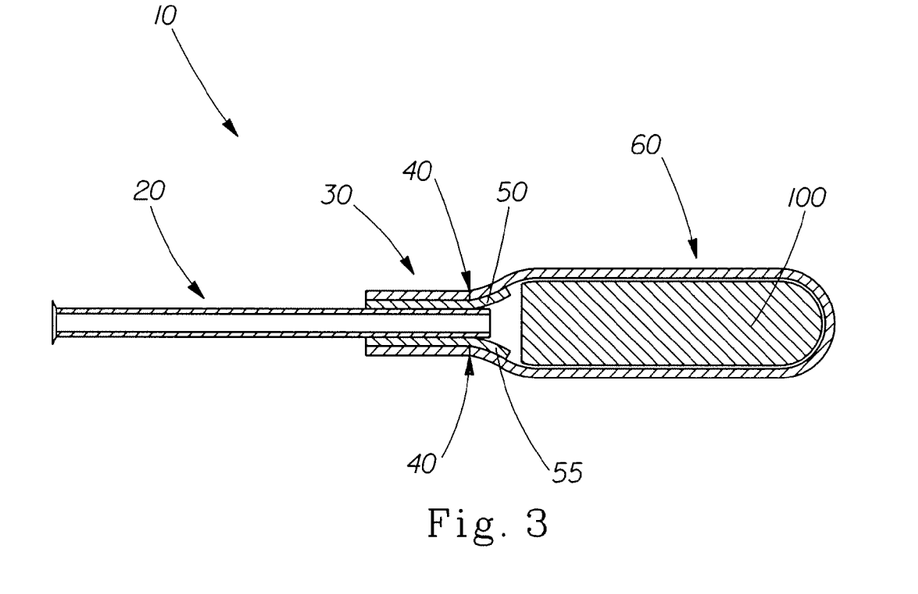
FIG. 3 is a cross-sectional view of one embodiment of the present invention.

FIG. 3 shows a cross-sectional view of one embodiment of the invention. The applicator 10 shown has a plunger 20, a grip portion 30, an inner support 50, and a barrel portion 60. A tampon 100 can be contained within the barrel portion 60 prior to depression of the plunger 20. As shown in FIG. 3, the grip portion 30 can be non-contiguous with the barrel portion 60, such as, e.g., separated by a split 40. In this embodiment, the grip portion 30 is rotatably connected to the inner support 50 and the inner support 50 is securely connected to the barrel portion 60 via one or more flanges 55. In addition, or alternatively, the inner support 50 can be rotatably connected to the barrel portion 60 and/or the grip portion 30 can be securely connected to the inner support 50. Therefore, in certain embodiments, the grip portion 30 and the inner support 50 are securely connected and can rotate relative to the barrel portion 60. In other embodiments, the inner support 50 remains stationary with respect to the barrel portion 60 and the grip portion 30 rotates with respect to the barrel portion 60 and with respect to the inner support 50. In addition, the applicator can have more than one inner support 50.

Figure 4:
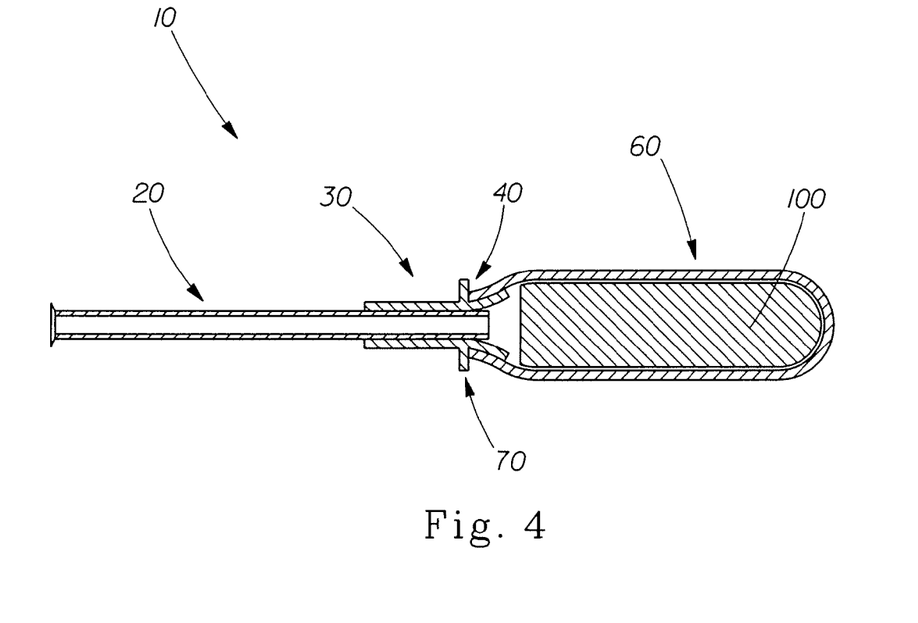
FIG. 4 is a cross-sectional view of one embodiment of the present invention.

FIG. 4 shows a cross-sectional view of one embodiment of the invention. The applicator 10 shown has a plunger 20, a grip portion 30, and a barrel portion 60. A tampon 100 can be contained within the barrel portion 60 prior to depression of the plunger 20. In this embodiment, the grip portion 30 is rotatably connected to the barrel portion 60. As shown in FIG. 4, the grip portion 30 includes a finger stop 70 that can, for example, reduce contact between the user's fingers and the barrel portion 60 when the user is holding the grip portion 30. The finger stop 70 can prevent the user from inadvertently touching the barrel portion 60 and providing friction that can decrease rotation while the user is holding the grip portion 30 and thus can allow for improved rotation of the grip portion 30 with respect to the barrel portion 60. The finger stop 70 can be integral with the grip portion 30, or, alternatively, the finger stop 70 can be a separate element connected to the grip portion 30. In certain embodiments, the finger stop 70 can be separated from the barrel portion 60 by a split 40. Alternatively, the finger stop 70 can be attached to the barrel portion 60. In certain embodiments, the finger stop 70 can be attached to the barrel portion 60 and separated from the grip portion 30.

Figure 5:
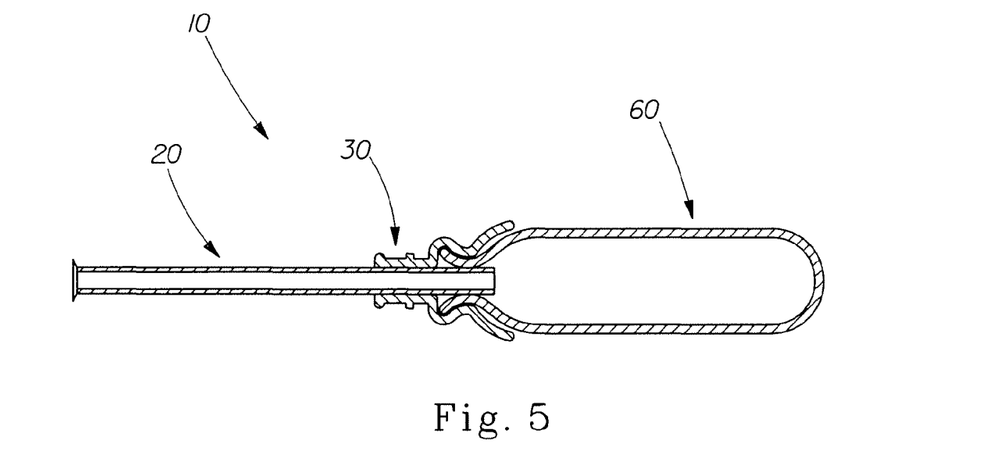
FIG. 5 is a cross-sectional view of one embodiment of the present invention.
Figure 6:
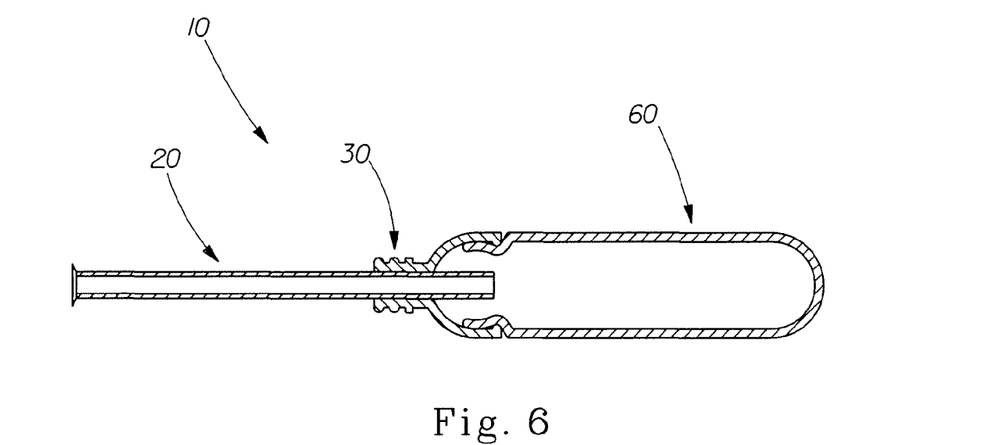
FIG. 6 is a cross-sectional view of one embodiment of the present invention.
Figure 7:
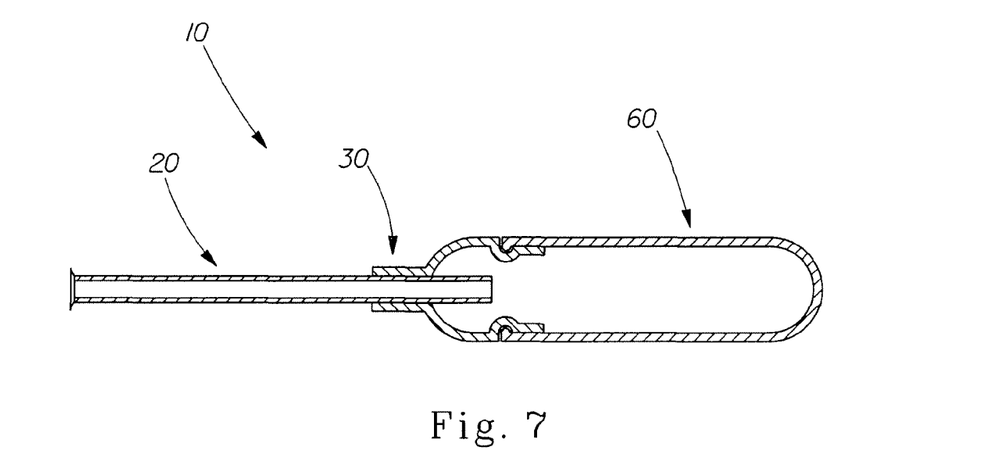
FIG. 7 is a cross-sectional view of one embodiment of the present invention.

FIGS. 5-7 show cross-sectional views of exemplary embodiments of the present invention. In each embodiment shown, the applicator 10 has a plunger 20, a grip portion 30, and a barrel portion 60. As shown in FIGS. 5-7, the grip portion 30 can be rotatably connected to the barrel portion 60. The grip portion 30 can be rotatably connected to the barrel portion 60 in any suitable manner. For example, the grip portion 30 can be rotatably connected to the barrel portion 60 such that the grip portion 30 is attached in the axial direction relative to the direction of tampon insertion, but is rotatable with respect to the barrel portion 60. Suitable connecting means include, for example, one or more protrusions, indentations, tabs, channels, flanges, rims, rings, edges, ribs, and/or collars, or other suitable means for rotatably connecting the barrel portion 60 to the grip portion 30. As shown in FIGS. 5-7, in certain embodiments, the grip portion 30 can attach to the barrel portion 60, such as, e.g., via a combination of protrusions and indentations that can join the barrel portion 60 to the grip portion 30 in a manner that allows rotation of the grip portion 30 about the barrel portion 60. In certain embodiments, the grip portion 30 can attach to the barrel portion 60 via one or more indentations on the barrel portion 60 and one or more protrusions on the grip portion 30. Alternatively, or in addition, the grip portion 30 can attach to the barrel portion 60 via one or more protrusions on the barrel portion 60 and one or more indentations on the grip portion 30. In certain embodiments, the barrel portion 60 and the grip portion 30 can attach together using one or more protrusions and one or more indentations on the barrel portion 60 and on the grip portion 30.

Figure 8:
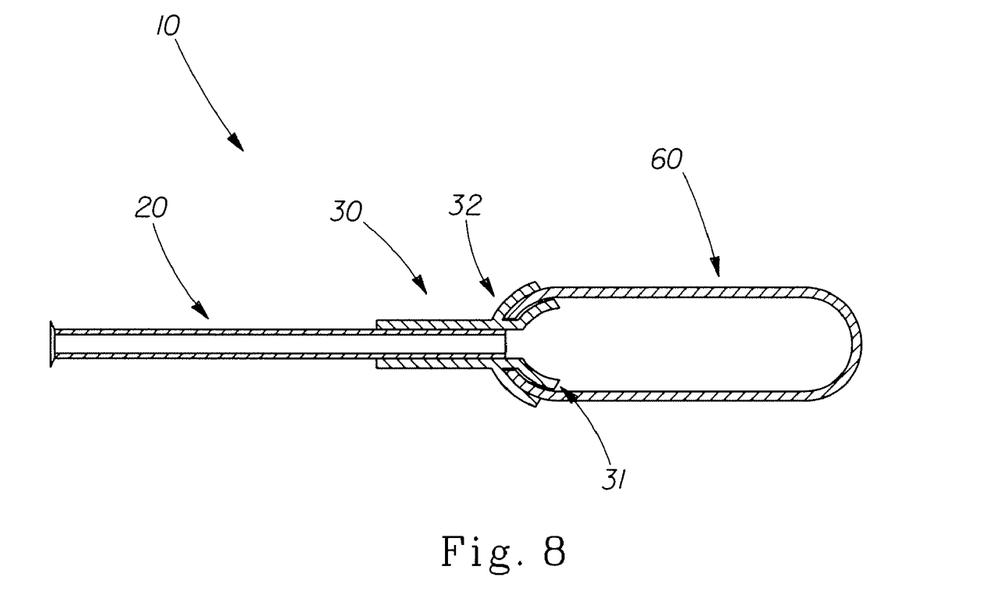
FIG. 8 is a cross-sectional view of one embodiment of the present invention.

FIG. 8 shows a cross-sectional view of one embodiment of the present invention. The applicator 10 has a plunger 20, a grip portion 30, and a barrel portion 60. The grip portion 30 can be rotatably connected to the barrel portion 60 via one or more flanges 31. As shown in FIG. 8, the grip portion 30 can include one or more finger shields 32 that can function to provide a finger stop that can, for example, reduce contact between the user's fingers and the barrel portion 60 when the user is holding the grip portion 30.

Figure 9:
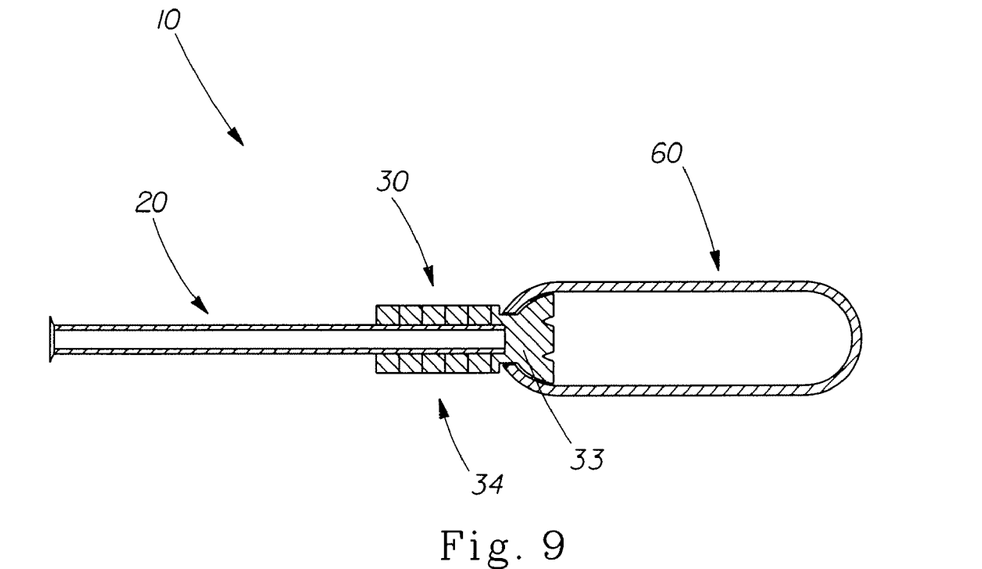
FIG. 9 is a cross-sectional view of one embodiment of the present invention.

FIG. 9 shows a cross-sectional view of one embodiment of the present invention. The applicator 10 has a plunger 20, a grip portion 30, and a barrel portion 60. As shown in FIG. 9, in this embodiment, the grip portion 30 can have an inner portion 33 and an outer portion 34. All or a portion of the grip portion 30 can be formed from a flexible material, such that in certain embodiments, the inner portion 33 of the grip portion can be displaced within the barrel portion 60 such that the grip portion 30 can be rotatably connected to the barrel portion 60. In certain embodiments, all or a portion of the grip portion 30 can be compressed, the inner portion 33 of the grip portion can be displaced within the barrel portion 60, and the all or a portion of the grip portion 30 that was compressed can expand within the barrel portion 60 such that the grip portion 30 is rotatably connected to the barrel portion 60.

Figure 10:
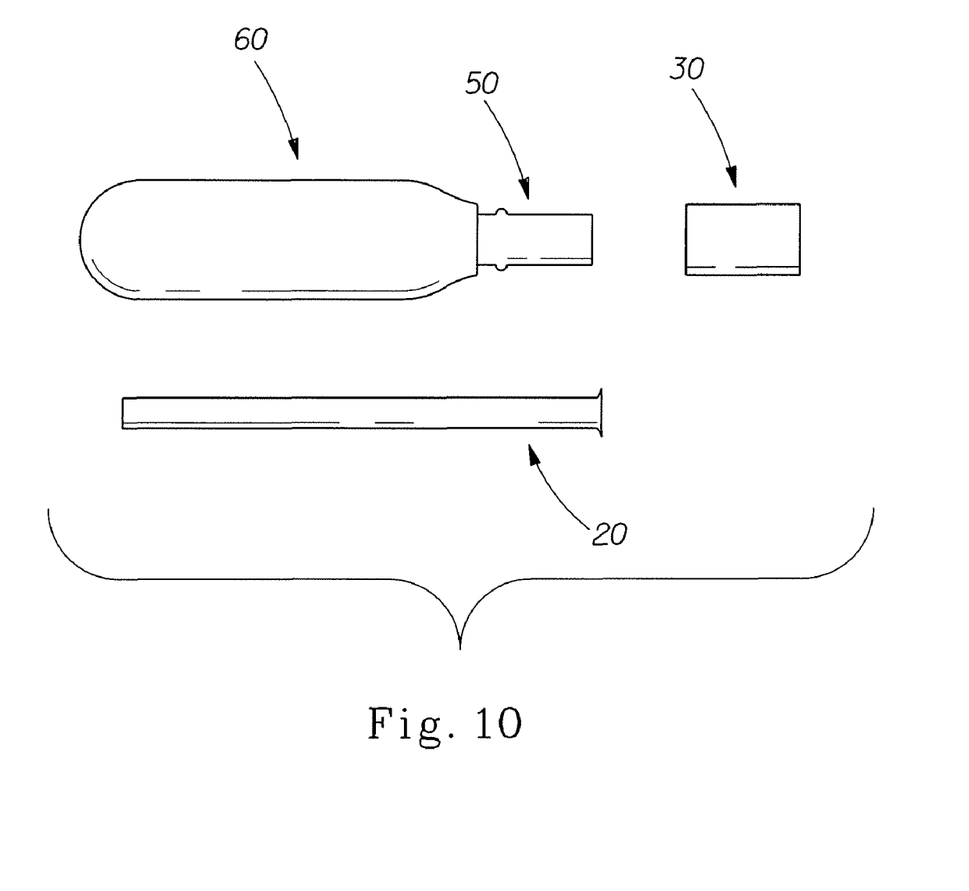
FIG. 10 is a plan view of one embodiment of the present invention.

FIG. 10 shows a plan view of components of one embodiment of the present invention. The applicator can include a plunger 20, a grip portion 30, an inner support 50, and a barrel portion 60. As shown in FIG. 10, in certain embodiments, the inner support 50 can be attached to the barrel portion 60 prior to assembly of the applicator. For example, the inner support 50 can be joined to the barrel portion 60, or, alternatively, the inner support 50 can be formed as a contiguous piece of the barrel portion 60. To assemble the applicator 10 shown in FIG. 10, the grip portion 30 can be rotatably connected to the inner support 50 and the plunger 20 can be inserted through the grip portion 30 and the inner support 50 into the barrel portion 60. In other embodiments, the inner support 50 can be formed as an integral piece with the grip portion 30.

Figure 11A:
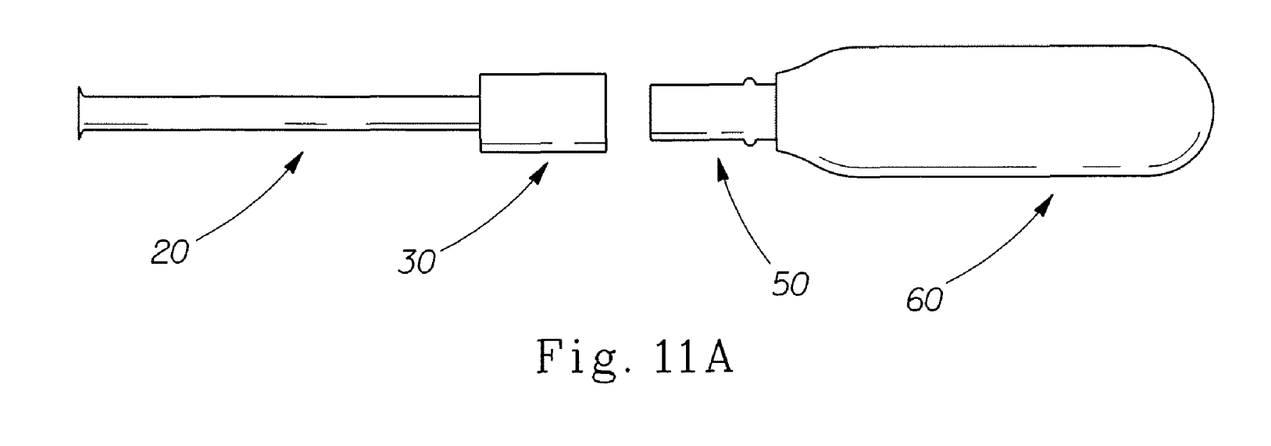
FIG. 11A is a plan view of one embodiment of the present invention.
Figure 11B:
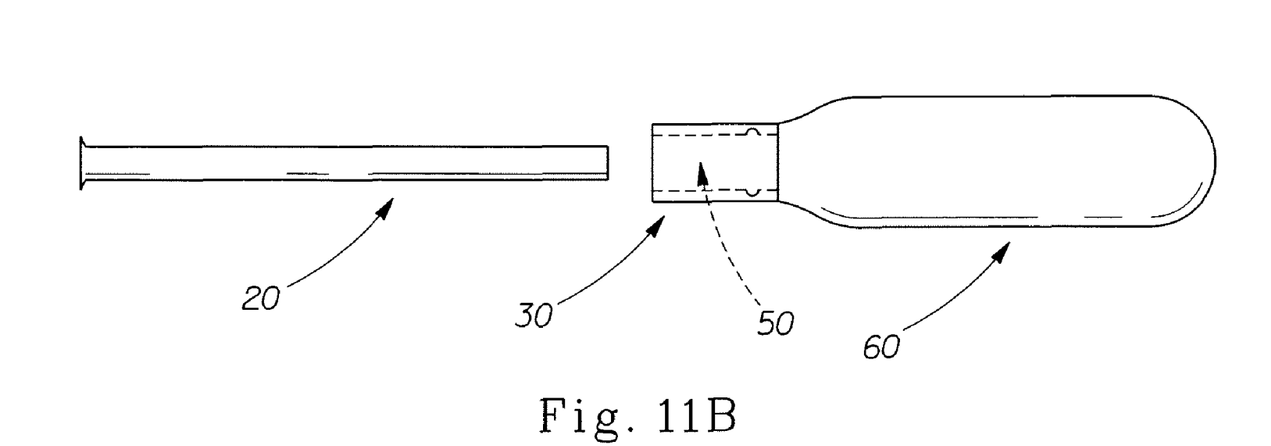
FIG. 11B is a plan view of one embodiment of the present invention.

FIGS. 11A and 11B show plan views of components of one embodiment of the present invention. The applicator can include a plunger 20, a grip portion 30, an inner support 50, and a barrel portion 60. As shown in FIG. 11A, in certain embodiments, the grip portion 30 can be attached to the plunger 20 prior to assembly of the applicator, such as, e.g., by forming the grip portion 30 as attached to the plunger 20. To assemble the applicator 10 shown in FIG. 11A, the grip portion 30 and plunger 20 can be rotatably connected to the inner support 50. The plunger 20 can be adapted to release from the grip portion 30 after assembly, such as, e.g., by the application of pressure along the direction of insertion. As shown in FIG. 11B, in certain embodiments, the grip portion 30 can be attached to the inner support 50 prior to assembly of the applicator. To assemble the applicator 10 shown in FIG. 11B, the plunger 20 can be inserted through the grip portion 30 and inner support 50 into the barrel portion 60. In certain embodiments, the grip portion 30 can be formed as attached to the inner support 50. The grip portion 30 can be formed as rotatably connected to the inner support 50, or, alternatively, the grip portion 30 can be formed securely connected to the inner support 50 and can be adapted to become rotatably connected to the inner support 50, such as, e.g., upon the application of force to the applicator.

Figure 12:
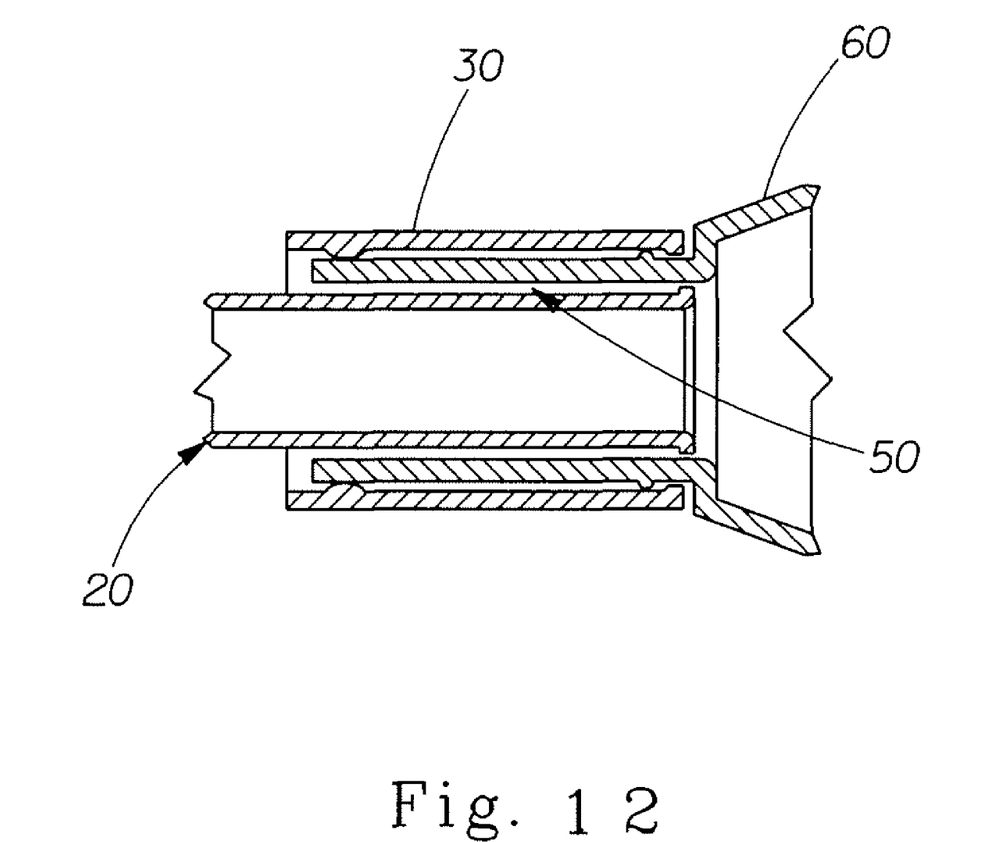
FIG. 12 is a cross-sectional view of one embodiment of the present invention.

FIG. 12 shows a cross-sectional view of a portion of one embodiment of the present invention. In this embodiment, the applicator includes a plunger 20, a grip portion 30, an inner support 50, and a barrel portion 60. As shown in FIG. 12, the inner support 50 is connected to the barrel portion 60 and the grip portion 30 is rotatably connected to the inner support 50, such as, e.g., by a combination of protrusions and indentations.

As such, the applicator can comprise a barrel portion, a grip portion, and a plunger, wherein the barrel portion rotates relative to the grip portion, such as, e.g., wherein the barrel portion of the applicator can rotate under body pressure relative to the grip portion to properly orient a feminine hygiene product within a user's vagina. In certain embodiments, the feminine hygiene product can include a tampon that provides increased leakage protection upon proper orientation in the vagina, such as, e.g., a tampon with non-uniform expansion, such as, e.g., a tampon having improved widthwise expansion compared to, for example, a tampon that can expand generally uniformly, such as, e.g., uniformly in more than one dimension. The feminine hygiene product can be inserted into a user's body using an applicator as described herein such that the applicator positions the tampon with the widthwise expansion aligned with the width of the vagina. For instance, the user can grasp the applicator by placing her fingers on the grip portion, insert the barrel portion containing the feminine hygiene product into her vagina, depress the plunger to expel the product from the barrel portion into her vagina, and remove the applicator. If the user inserts the barrel portion such that the portion of the feminine hygiene product having the largest potential widthwise expansion is oriented in a front to back manner or at an angle, the barrel portion can rotate within the user's body so that the feminine hygiene product is in the correct position, for example, with the largest width in a side to side position, such as, e.g., with the maximum expansion of the feminine hygiene product aligned with the maximum width of the vagina. Because the barrel portion can rotate relative to the grip portion, the user may not even be aware that the applicator and tampon are rotating into the proper orientation, as the grip portion can remain stationary within her grasp.

The barrel portion can be constructed from any suitable material. Suitable materials include, for example, polyethylene, polypropylene, polybutylene, polystyrene, polyvinylchloride, polyacrylate, polymethacrylate, polyacrylnitril, polyacrylamide, polyamide, nylon, polyimide, polyester, polycarbonate, ethylene vinyl acetate, polyurethane, silicone, derivatives thereof, copolymers thereof, mixtures thereof, paper, paperboard, cardboard, cellulose, such as, e.g., molded cellulose, any combinations thereof, or any suitable smooth plastic material. Examples of suitable materials are disclosed in, e.g., U.S. Pat. Nos. 5,346,468 and 5,558,631. In certain embodiments, additives can be included in the material to alter or enhance certain material properties. Suitable additives include, for example, mold release agents, slip agents, surface energy modifiers, pearlescent agents, and/or any other suitable additives. In certain embodiments, the barrel portion can be coated with a substance to give it a high slip characteristic, such as, e.g., with wax, polyethylene, a combination of wax and polyethylene, cellophane, clay, mica, and other lubricants that can facilitate comfortable insertion. Alternatively, or in addition, the barrel portion can include a textured surface. Texture can be provided in any suitable manner, such as, e.g., by designing texture into or adding texture to the barrel.

The barrel portion can be sized and configured to house a feminine hygiene product, such as, e.g., an absorbent tampon and/or pessary. In certain embodiments, the size of the barrel portion can be determined primarily by the dimensions of the feminine hygiene product. For example, the barrel portion can have inner diameters of about 5.0 millimeters to about 22.0 millimeters and a wall thickness of about 0.2 millimeter to about 2.0 millimeters. The inner diameter of the barrel portion can be greater than the diameter of the feminine hygiene product to prevent the barrel portion from interfering with the expulsion of the feminine hygiene product from the barrel portion. In certain embodiments, the inner diameter of the barrel portion can have varying diameters and shapes to conform to the profiled shape of the enclosed feminine hygiene product, such as, e.g., a tampon. The barrel portion can have a length sufficient to house the feminine hygiene product prior to the expulsion of the feminine hygiene product from the applicator into the vagina.

The barrel portion can be of any suitable cross-sectional shape. In certain embodiments, the barrel portion can include a generally non-circular cross-sectional shape, such as, e.g., oval, rectangular, elliptical, oblate, or other suitable shapes. The barrel portion can have a cross-sectional shape that has a greater thickness than width or vice versa. In certain embodiments, the barrel portion can have a substantially uniform cross-section, such as, e.g., having the same cross-section along the length. In other embodiments, the barrel portion can have varying cross-sectional shapes and/or cross-sectional sizes, such as, e.g., a barrel portion having a smaller cross-sectional area near the insertion end of the barrel and a larger cross-sectional area near the opposite end and/or a barrel portion having a primarily non-circular cross-sectional shape and also having one or more circular cross-sections. For example, in certain embodiments, a barrel portion having a generally non-circular cross-sectional shape can have greater than about 50% of the cross-sections having a non-circular cross-sectional shape, such as, e.g., greater than about 60%, greater than about 70%, greater than about 80%, greater than 90%, and/or about 100% of the cross-section having a non-circular cross-sectional shape. In certain embodiments, substantially the entire barrel portion can have a generally non-circular cross-sectional shape, with the cross-sectional shape changing to circular proximal to the grip portion.

The insertion end of the barrel portion can be open-end or closed-ended. In certain embodiments, the insertion end of the barrel portion can include petals, corrugations, pleats, a film cap, or other means for covering the barrel portion prior to explusion of the tampon. In certain embodiments, the feminine hygiene product can be loaded into the barrel portion prior to covering the insertion end of the barrel portion. Alternatively, the insertion end of the barrel portion can be covered prior to loading the feminine hygiene product into the barrel portion. In certain embodiments, the barrel portion can have an oval cross-sectional shape and the insertion end can include petals, such as, an even number of petals. In certain embodiments, the lines between petals can be parallel to the axes of the oval.

The grip portion can be constructed from any suitable material. Suitable materials include, for example, polyethylene, polypropylene, polybutylene, polystyrene, polyvinylchloride, polyacrylate, polymethacrylate, polyacrylnitril, polyacrylamide, polyamide, nylon, polyimide, polyester, polycarbonate, ethylene vinyl acetate, polyurethane, silicone, derivatives thereof, copolymers thereof, mixtures thereof, paper, paperboard, cardboard, any combinations thereof, or any suitable smooth plastic material. In certain embodiments, additives can be included in the material to alter or enhance certain material properties. Suitable additives include, for example, mold release agents, slip agents, surface energy modifiers, pearlescent agents, and/or any other suitable additives.

The grip portion can provide for secure handling of the applicator. The perimeter of the grip portion can be any suitable shape, such as, for example, oval, circular, arc, concave, cone convex, diamond, line, polygon, rib, square, triangle, rectangular, or any combination thereof. The grip portion can include projections, depressions, texturing, embossments, grooves, treads, and/or raised surfaces. Such surfaces can be created by impressing or compressing the surfaces. In certain embodiments, the grip portion can include one or more flattened sides and/or one or more spaces for a decorative marking or a character. In addition, or alternatively, the surfaces of the grip portion can include a material that can provide a frictional resistance for the user's fingers during the insertion of the tampon applicator into the body. Suitable materials that can provide friction include, for example, abrasive materials, high wet coefficient of friction materials, pressure sensitive adhesives, or any combinations thereof. In certain embodiments, the surfaces of the grip portion can include a material that can improve the feel of the grip to a user, such as, e.g., rubber or foam. In certain embodiments, the grip portion shape can correspond to the barrel portion shape, such as, e.g., an oval grip portion with an oval barrel portion. Alternatively, the grip portion can be a different shape than the barrel portion, such as, e.g., a circular grip portion with an oval barrel portion.

The applicator can include one or more inner supports. In certain embodiments, the inner support can be securely connected to the barrel portion and rotatably connected to the grip portion. Alternatively, or in addition, the inner support can be rotatably connected to the barrel portion and securely connected to the grip portion. In other embodiments, the applicator can include two or more inner supports, wherein the first inner support is securely connected to the barrel portion and rotatably connected to the grip portion and the second inner support is rotatably connected to the barrel portion and securely connected to the grip portion. The inner support can be formed separately from the barrel portion and/or the grip portion or the inner support can be formed integral to the barrel portion and/or the grip portion. In certain embodiments, the inner support can have a circular cross-sectional shape, such as, e.g., to facilitate rotation of the barrel portion relative to the grip portion.

The plunger can be constructed from any suitable material. Suitable materials include, for example, polyethylene, polypropylene, polybutylene, polystyrene, polyvinylchloride, polyacrylate, polymethacrylate, polyacrylnitril, polyacrylamide, polyamide, nylon, polyimide, polyester, polycarbonate, ethylene vinyl acetate, polyurethane, silicone, derivatives thereof, copolymers thereof, mixtures thereof, paper, paperboard, cardboard, any combinations thereof, or any suitable smooth plastic material. Suitable plungers are disclosed in, e.g., U.S. Pat. No. 5,346,468 and U.S. Pat. No. 5,558,631. In certain embodiments, additives can be included in the material to alter or enhance certain material properties. Suitable additives include, for example, mold release agents, slip agents, surface energy modifiers, pearlescent agents, and/or any other suitable additives.

The plunger can be hollow or solid. In certain embodiments, the plunger can have a hollow interior, a first end, and a second end opposed to the first end. The first end is the portion of the plunger that pushes against the tampon during the expulsion of the tampon from the barrel portion. The second end is the portion of the plunger in which the axial force is applied to expel the tampon from the barrel portion. In certain embodiments, the plunger can have a locking mechanism, such as, e.g., a locking mechanism that retains the plunger within the barrel portion and/or grip portion of the applicator prior to depression of the plunger and expulsion of the tampon. Examples of such locking mechanisms are described in, for example, U.S. Pat. Nos. 6,019,744 and 6,450,986.

The plunger can be any suitable shape. Suitable shapes include, for example, shapes that can work effectively to aide in the expulsion of the tampon from the tampon applicator. Suitable cross-sectional shapes include, e.g., circular, oval, flattened circular, elliptical, and any combinations thereof. In certain embodiments, the plunger shape can correspond to the barrel portion shape, such as, e.g., an oval plunger with an oval barrel portion. Alternatively, the plunger can be a different shape than the barrel portion, such as, e.g., a plunger with a circular cross-section with an oval barrel portion. In certain embodiments, the plunger cross-sectional shape can correspond to the grip portion cross-sectional shape, such as, e.g., a circular plunger with a circular grip portion. Alternatively, the plunger can be a different cross-sectional shape than the grip portion, such as, e.g., a plunger with a circular cross-section with an oval grip portion. The plunger can also be the same cross-sectional shape as the grip portion and a different cross-sectional shape than the barrel portion; a different cross-sectional shape from the grip portion and the same cross-sectional shape as the barrel portion; or a different cross-sectional shape from the grip portion and a different cross-sectional shape from the barrel portion. In certain embodiments, the plunger can include more than one cross-sectional shape along the length. For example, in certain embodiments, the plunger can include a circular cross-sectional shape at one end and change to a cross-sectional shape that is the same as the cross-sectional shape of the feminine hygiene product, such as, e.g., a tampon, on the end nearest the feminine hygiene product. In certain embodiments, the plunger can maintain a cross-sectional shape along the length but the diameter of the shape can vary along the length of the plunger.

In certain embodiments, the plunger can be an optional component for use with the applicator. For example, the applicator can be fully functional if the plunger is omitted, i.e., if a user must insert and push the feminine hygiene product through the tampon applicator digitally.

In certain embodiments, at least a portion of the applicator can contact and/or conform to at least a portion of the surface of the tampon. Rigid insertion end structures can be shaped in a suitable manner, such as, e.g., by injection molding, or by reshaping in a secondary process to provide at least a degree of profiled shape observation. Alternatively, insertion ends of applicators made from flexible or pliable materials, such as films, paper and flexible wovens or non-wovens, can also be used. Such flexible or pliable insertion ends include those which partially or fully enclose the tampon comprising a "sleeve" or a "tube," such as, e.g., in U.S. Pat. Nos. 2,922,422 and 2,922,423; a "sheath," such as, e.g., in U.S. Pat. Nos. 2,092,427 and 3,749,093; a "barrel," such as, e.g., in U.S. Pat. No. 5,135,475; a "bag," such as, e.g., in U.S. Pat. No. 3,358,686; or a "film enclosure," such as, e.g., in U.S. Pat. No. 4,610,659.

In certain embodiments, the applicators can be designed for use with tampons that have a non-uniform expansion, such as, e.g., tampons having greater expansion in the width direction than in the length direction. Suitable tampons can have any suitable cross-sectional shape, such as, e.g., circular, generally circular, circular with flattened sides, elliptical, oval, or any other suitable cross-sectional shape. Exemplary tampons having a circular cross-section are described in, e.g., U.S. Pat. Nos. 6,837,882; 6,740,070; 6,682,513; 6,599,279; 6,554,814; and 6,258,075.

Alternatively, or in addition, the applicators can be designed for use with tampons having widthwise expansion and a non-circular cross-section, such as, e.g., a tampon having a substantially oval cross-sectional shape, such as a tampon that is formed having an oval cross-sectional shape. In certain embodiments, a generally non-circular cylindrical tampon can include a tampon having one or more circular cross-sections, wherein the tampon primarily includes non-circular cross-sectional shapes. For example, in certain embodiments, a generally non-circular cylindrical tampon can have greater than about 50% of the cross-sections having a non-circular cross-sectional shape, such as, e.g., greater than about 60%, greater than about 70%, greater than about 80%, greater than about 90%, and/or about 100% of the cross-section having a non-circular cross-sectional shape. The tampon can provide an improved non-uniform expansion, such as, e.g., improved widthwise expansion. In certain embodiments, the tampon can comprise a pledget that can be compressed to form a tampon with a substantially oval cross-section. Exemplary tampons are described in U.S. patent application Ser. No. 11/703,946, to Hasse, et al., titled "Self-Orienting Tampon Having Improved Aspect Ratio," filed on Feb. 7, 2007.

In certain embodiments, the applicator can be constructed from one piece. For example, the applicator can have a barrel portion, a grip portion, and a plunger that are molded or otherwise constructed as one piece. The grip portion can be designed to rotate with respect to the barrel portion as constructed or can be made to rotate with respect to the barrel portion upon application of force to the applicator. The barrel portion, grip portion, and/or plunger can be connected to one another at predetermined breaking points and/or can be formed within one mold such that the applicator emerges from the mold assembled into one piece having a grip portion, a barrel portion, and a plunger.

In certain embodiments, the applicator can be constructed from two separate pieces. For example, the applicator can be constructed from one piece that forms the barrel portion and one piece that forms the grip portion and plunger. The piece including the grip portion and plunger can be attached to the barrel portion. In certain embodiments, the grip portion and plunger can be connected by tabs or flanges that can be broken when pressure is applied to the plunger. Thus, the piece including the grip portion and plunger can be attached to the barrel portion and the plunger can be depressed, separating the plunger and grip portion. The plunger and grip can be separated at any suitable time, such as, e.g., prior to or during packaging, and/or by the user prior to or during use of the applicator. In certain embodiments, the applicator can be constructed from one piece that forms the barrel portion and grip portion and one piece that forms the plunger. The barrel portion and grip portion can be connected at predetermined breaking points such that the grip portion can be made to rotate with respect to the barrel portion when force is applied to the grip portion. The plunger and tampon can be added to the applicator at any suitable time. In certain embodiments, the barrel portion and the grip portion can be connected at predetermined breaking points such that the grip portion can be made to rotate with respect to the barrel portion when force is applied by a user.

In certain embodiments, the applicator can be constructed from at least three separate pieces. For example, the applicator can be constructed from at least a barrel portion, a grip portion, and a plunger that are prepared separately, such as, e.g., by injection molding. The grip portion can be connected to the barrel portion such that it is rotatable with respect to the barrel portion, and the plunger can be inserted into the barrel portion either before or after the grip portion is attached to the barrel portion. The tampon can be loaded at any suitable time. In certain embodiments, the barrel portion can comprise petals that can be formed either before or after the tampon is loaded into the barrel portion. In certain embodiments, the applicator can be constructed from four or more separate pieces, such as, e.g., a barrel portion, a grip portion, a plunger, and/or an inner support.

In certain embodiments, the barrel portion can fully rotate with respect to the grip portion, such as, e.g., the barrel portion can rotate 360° with respect to the grip portion. Alternatively, or in addition, the barrel portion can partially rotate with respect to the grip portion, such as, e.g., the barrel portion can rotate less than about 360°, such as, e.g., about 300°, about 240°, about 180°, about 120°, about 90°, or about 45°, or any other suitable amount. In certain embodiments, rotation of the barrel portion with respect to the grip portion can be signaled by an audible sound, such as, e.g., a click.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An applicator comprising: a barrel portion comprising an insertion end, a feminine hygiene product disposed within the barrel portion, a grip portion for gripping the applicator during insertion of the barrel portion into the body and for expulsion of the feminine hygiene product from the barrel portion, and a plunger; the barrel portion being rotatably connected to the grip portion wherein the barrel portion is rotatable relative to the grip portion, and the barrel portion being securely connected to the grip portion in an axial direction wherein the grip portion is substantially prevented from moving towards the insertion end.

2. The applicator of claim 1, wherein the barrel portion is rotatably connected to the grip portion by one or more means selected from the group consisting of: protrusions, indentations, tabs, channels, flanges, rims, rings, edges, ribs, collars, or combinations thereof.

3. The applicator of claim 1, wherein the grip portion is indirectly attached to the barrel portion.

4. The applicator of claim 3, the applicator having at least one inner support connected to the barrel portion.

5. The applicator of claim 4, wherein the at least one inner support is securely connected to the barrel portion and rotatably connected to the grip portion, the barrel portion and the at least one inner support being adapted to rotate relative to the grip portion.

6. The applicator of claim 5, wherein the at least one inner support is integral to the barrel portion.

7. The applicator of claim 1, the applicator having at least one inner support connected to the barrel portion, the at least one inner support having a substantially circular cross-section.

8. The applicator of claim 1, the plunger or grip portion having a substantially circular cross-sectional shape.

9. The applicator of claim 1, the barrel portion having a substantially oval cross-sectional shape.

10. The applicator of claim 1, wherein the feminine hygiene product is a tampon having a non-uniform expansion capability.

* * * * *